US007670307B2

(12) United States Patent
Chitwood et al.

(10) Patent No.: US 7,670,307 B2

(45) Date of Patent: Mar. 2, 2010

(54) CERVICAL TRACTION/STRETCH DEVICE KIT

(75) Inventors: Nathan Chitwood, Kalispell, MT (US); Susan Nickell, Kalispell, MT (US)

(73) Assignee: International Rehabilitative Sciences, Inc., Vancouver, WA (US)

( * ) Notice: Subject to any disclaimer, the term of this patent is extended or adjusted under 35 U.S.C. 154(b) by 63 days.

(21) Appl. No.: 12/069,328

(22) Filed: Feb. 8, 2008

(65) Prior Publication Data

US 2009/0204046 A1 Aug. 13, 2009

(51) Int. Cl.
*A61F 5/00* (2006.01)

(52) U.S. Cl. .......................... 602/13; 602/18; 128/869; 128/DIG. 23

(58) Field of Classification Search .................. 602/17, 602/18, 13; 128/DIG. 23; 5/622, 636, 637
See application file for complete search history.

(56) References Cited

U.S. PATENT DOCUMENTS

| | | | | |
|---|---|---|---|---|
| 3,343,532 | A | 9/1967 | Zumaglini | |
| 4,058,112 | A | 11/1977 | Johnson | |
| 4,099,523 | A | 7/1978 | Lowrey | |
| 4,508,109 | A | 4/1985 | Saunders | |
| 4,543,947 | A | 10/1985 | Blackstone | |
| 4,617,691 | A | 10/1986 | Monti et al. | |
| 4,702,235 | A | 10/1987 | Hong | |
| 4,771,493 | A | 9/1988 | Park | |
| 4,805,603 | A | 2/1989 | Cumberland | |
| 4,832,007 | A | 5/1989 | Davis, Jr. et al. | |
| 4,850,003 | A | 7/1989 | Huebeck et al. | |
| 5,060,661 | A | 10/1991 | Howard | |
| 5,067,483 | A | 11/1991 | Freed | |
| 5,181,904 | A | 1/1993 | Cook et al. | |
| 5,243,722 | A | 9/1993 | Gusakov | |
| 5,382,226 | A | 1/1995 | Graham | |
| 5,403,266 | A | 4/1995 | Bragg et al. | |
| 5,441,781 | A | 8/1995 | Chitwood | |
| 5,454,781 | A | 10/1995 | Chitwood | |
| 5,569,176 | A | 10/1996 | Graham | |
| 5,575,295 | A * | 11/1996 | Khalsa et al. | 5/636 |
| 5,752,927 | A | 5/1998 | Rogachevsky | |
| 5,823,982 | A | 10/1998 | Park | |
| 5,916,185 | A * | 6/1999 | Chitwood | 602/18 |
| 6,289,538 | B1 | 9/2001 | Fidge | |
| 6,447,468 | B1 | 9/2002 | Hankins et al. | |

(Continued)

*Primary Examiner*—Michael A. Brown
(74) *Attorney, Agent, or Firm*—Blank Rome LLP

(57) ABSTRACT

The cervical traction/stretch device kit comprises a cervical traction/stretch device including an expandable bellows section which is made of non-elastic and non-stretchable material. The device further includes a shoulder section which can be fixed to or made integral with the bellows section. At least two, preferably three, interchangeable head sections are provided so that substantially all human head sizes can be supported by the device. Also provided is a head frame section which is releasably assembled with one of the head sections, the bellows section and the shoulder section to provide a cervical traction/stretch device. The bellows section, the shoulder section and the head section have aligned U-shaped openings therein adapted to receive and support a patient's neck. A pumping mechanism, preferably including an air pump and pressure relief structure are connected to the bellows section for pumping air into the bellows section for expanding the bellows section and for relieving or releasing air out of the bellows section. A triangular-in-cross-section base is provided in the kit for supporting the device at a small angle to the horizontal.

20 Claims, 6 Drawing Sheets

U.S. PATENT DOCUMENTS

| | | | |
|---|---|---|---|
| 7,048,705 B2 | 5/2006 | Pillai | |
| 7,070,573 B2 | 7/2006 | Axelsson | |
| 7,507,216 B2 * | 3/2009 | Buckman et al. | 602/32 |

* cited by examiner

CERVICAL TRACTION/STRETCH DEVICE KIT

BACKGROUND OF THE INVENTION

1. Field of the Invention

The present invention relates to a kit including a cervical traction/stretch device which is positioned under the neck of a user lying on a flat surface and between the shoulders and the head of the user and includes an expandable, but non-elastic and non-stretchable, bellows section, as well as a shoulder section, a head frame section and a head section. A hand operated air pump with an air pressure relief valve is connected to the bellows section for manually filling the bellows section and for expanding and contracting the bellows section thereby to stretch the neck and to release a stretching force on the neck. The kit includes at least two, preferably three, interchangeable head sections for accommodating substantially all human head sizes. Further, the kit includes a triangular-in-cross-section base stand for supporting the device at a small angle to the horizontal.

2. Description of the Related Art

Prior art cervical traction/stretch devices are disclosed in the following U.S. patents:

| U.S. Pat. No. | Patentee |
|---|---|
| 3,343,532 | Zumaglini |
| 4,058,112 | Johnson |
| 4,099,523 | Lowery |
| 4,508,109 | Saunders |
| 4,543,947 | Blackstone |
| 4,617,691 | Monti et al. |
| 4,702,235 | Hong |
| 4,771,493 | Park |
| 4,805,603 | Cumberland |
| 4,832,007 | Davis Jr. et al. |
| 4,850,003 | Huebeck et al. |
| 5,060,661 | Howard |
| 5,067,483 | Freed |
| 5,181,904 | Cook et al. |
| 5,243,722 | Gusakov |
| 5,382,226 | Graham |
| 5,403,266 | Bragg et al. |
| 5,441,781 | Chitwood |
| 5,454,781 | Chitwood |
| 5,569,176 | Grahm |
| 5,752,927 | Rogachevsky |
| 5,823,982 | Park |
| 5,916,185 | Chitwood |
| 6,289,538 | Fidge |
| 6,447,468 | Hankins et al. |
| 7,048,705 | Pillai |
| 7,070,573 | Axelsson |

The most pertinent prior art patents are the Chitwood U.S. Pat. Nos. 5,441,781, 5,454,781 and 5,916,184. This application is directed to improvements to the cervical/stretch devices disclosed in these patents and to a cervical/stretch device kit including new and improved elements.

SUMMARY OF THE INVENTION

According to the present invention there is provided a cervical traction/stretch device kit comprising a cervical traction/stretch device including an expandable bellows section which is made of non-elastic and non-stretchable material. The device further includes a shoulder section which can be fixed to or made integral with the bellows section. At least two, preferably three, interchangeable head sections are provided so that substantially all human head sizes can be supported by the device. Also provided is a head frame section which is releasably assembled with one of the head sections, the bellows section and the shoulder section to provide a cervical traction/stretch device. The bellows section, the shoulder section and the head section have aligned U-shaped openings therein adapted to receive and support a patient's neck. A pumping mechanism, preferably including an air pump and pressure relief structure are connected to the bellows section for pumping air into the bellows section for expanding the bellows section and for relieving or releasing air out of the bellows section. A triangular-in-cross-section base is provided in the kit for supporting the device at a small angle to the horizontal.

DESCRIPTION OF THE PREFERRED EMBODIMENTS OF THE INVENTION

Figure 1:
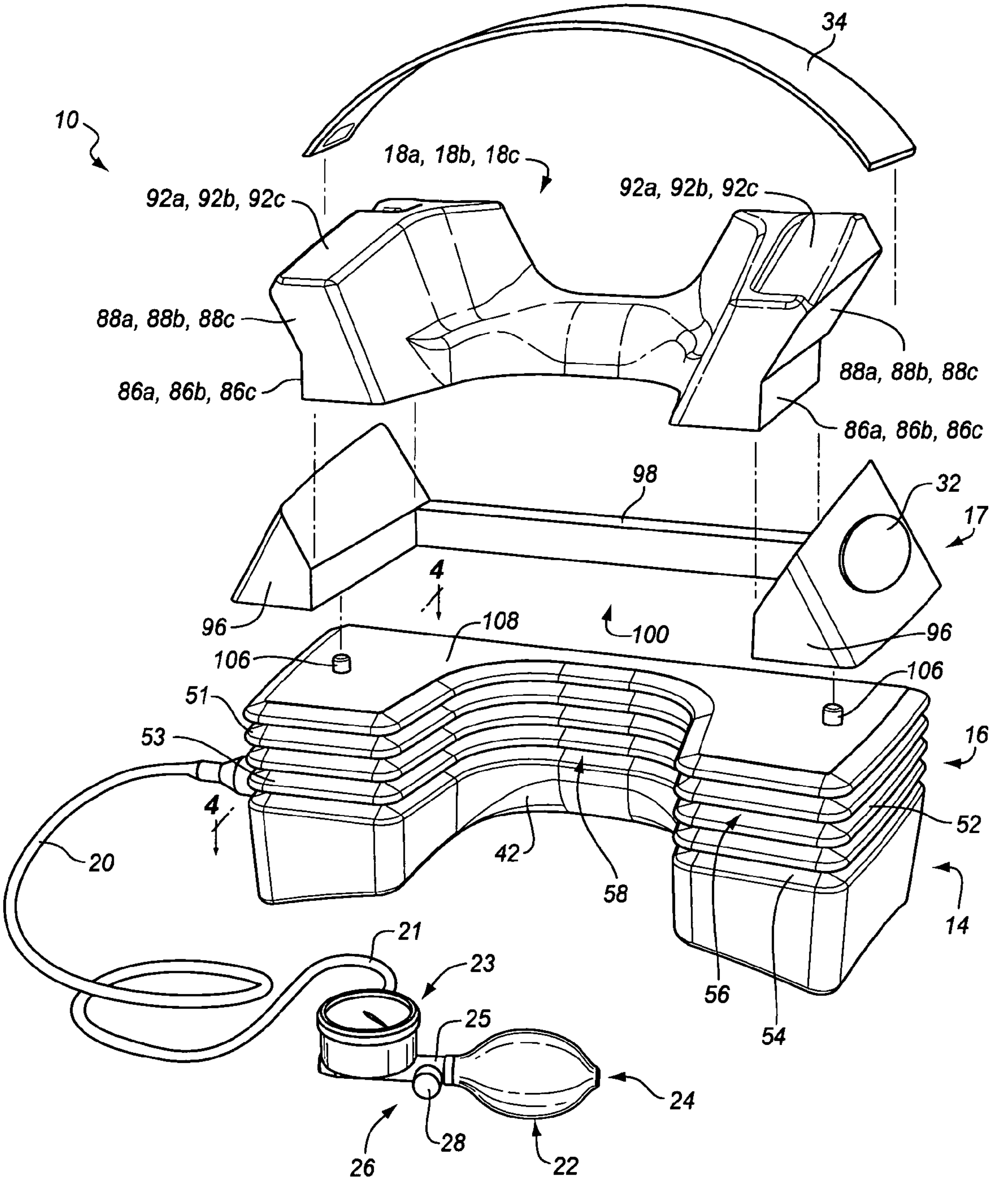
FIG. 1 is an exploded perspective front view of the cervical traction/stretch device constructed according to the teachings of the present invention.

Referring now to the drawings in greater detail, there is illustrated in FIG. 1, in an exploded perspective view, a cervical traction/stretch device 10 of a cervical traction/stretch device kit constructed according to the teachings of the present invention. The device 10 includes a shoulder section 14, a bellows section 16, a head frame section 17 and one of three head sections **18*a* (FIG. 5), 18*b* (FIG. 6) or 18*c* (FIG. 7**) forming parts of the kit.

The cervical traction/stretch device 10 further includes a tubing 20 connected to the bellows section 16 or through the shoulder section 14 as shown, and having, at an outer end 21 thereof, an air pump 22 in the form of a compressible bulb 22 for pumping the cervical traction/stretch device 10 with air. A pressure gauge 23 is provided between the tubing 20 and the pump 22. The compressible bulb 22 has, at its outer end, a one way inlet valve 24 which allows air to be sucked into the bulb 22, but does not allow air to flow out of the bulb 22 when it is compressed.

Adjacent to the bulb 22 and mounted to a coupling 25 carrying the pressure gauge is a relief valve 26 which comprises a knurled thumbscrew 28. When the thumbscrew 28 is rotated into the coupling 25, no air can escape from the cervical traction/stretch device 10 and when the thumbscrew 28 is threaded outwardly, the relief valve 26 is opened to allow compressed air to escape from the cervical traction/stretch device 10 through the tubing 20 and out of the relief valve 26.

In addition to the compressible bulb 22 and the tubing 20, the cervical traction/stretch device 10 includes, on either side of the head frame 17, loop and hook type fastening structure 32 of the type sold under the trademark VELCRO® and the device kit further includes a head strap 34 (FIG. 8) which is adapted to be received over a patient's head and secured to the head frame 17. The strap 34 has, on its inner surface thereof, a fabric texture which is adapted to attach to the fastening structures 32 on each side of the head frame 17 as will be described in greater detail hereinafter.

The shoulder section 14, the bellows section 16 and the head sections 18*a*, 18*b* or 18*c* each have various specially shaped curved surfaces for allowing the device 10 to create comfortable and therapeutic stretching to a patient's neck. These specially shaped curved surfaces are described in detail in U.S. Pat. No. 5,441,781, the disclosure of which is incorporated herein by reference.

The bellows section 16 is constructed with a plurality, e.g., four (4) undulations 51, 52, 53, 54 and 55 (FIG. 3) in the illustrated embodiment and is constructed and arranged to raise and support the cervical curve of a patient's neck during inflation.

Figure 3:
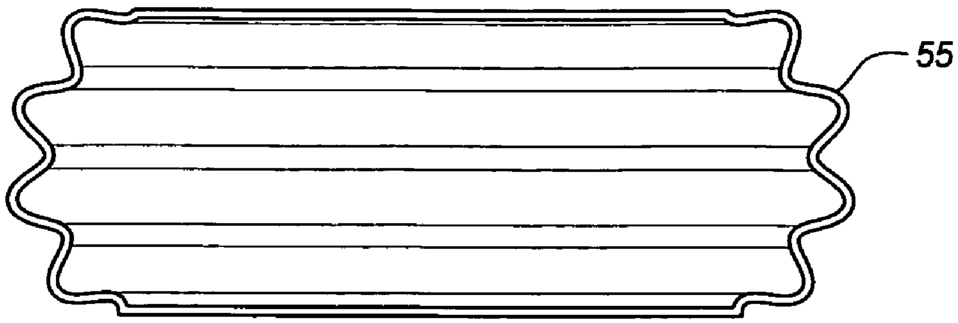
FIG. 3 PRIOR ART
FIG. 3 is a cross-sectional view through an inflated prior art bellows section of a prior art cervical traction/stretch device.

According to the teachings of the present invention, the bellows section 16, while being expandable by reason of the undulations 51-54, is made of non-elastic and non-stretchable material, preferably PVC, as opposed to a prior art elastic bellows section. This is important, since, as shown in FIG. 3, in a prior art elastic bellows 55 the material stretches laterally outwardly, sidewise, resulting in less traction or stretch force being applied on a patient's neck and causes erroneous pressure readings. In this respect, the pressure gauge may be reading a constant value for the pumped air pressure going into the stretching of the bellows section 55, leaving the patient to believe that he or she has reached a predetermined pressure value which is a maximum value for a creating a maximum stretch force. In one preferred embodiment, the shoulder section and bellows section are made integral from P130 Plastisol having a 70-80 durometer on the Shore A scale.

Figure 4:
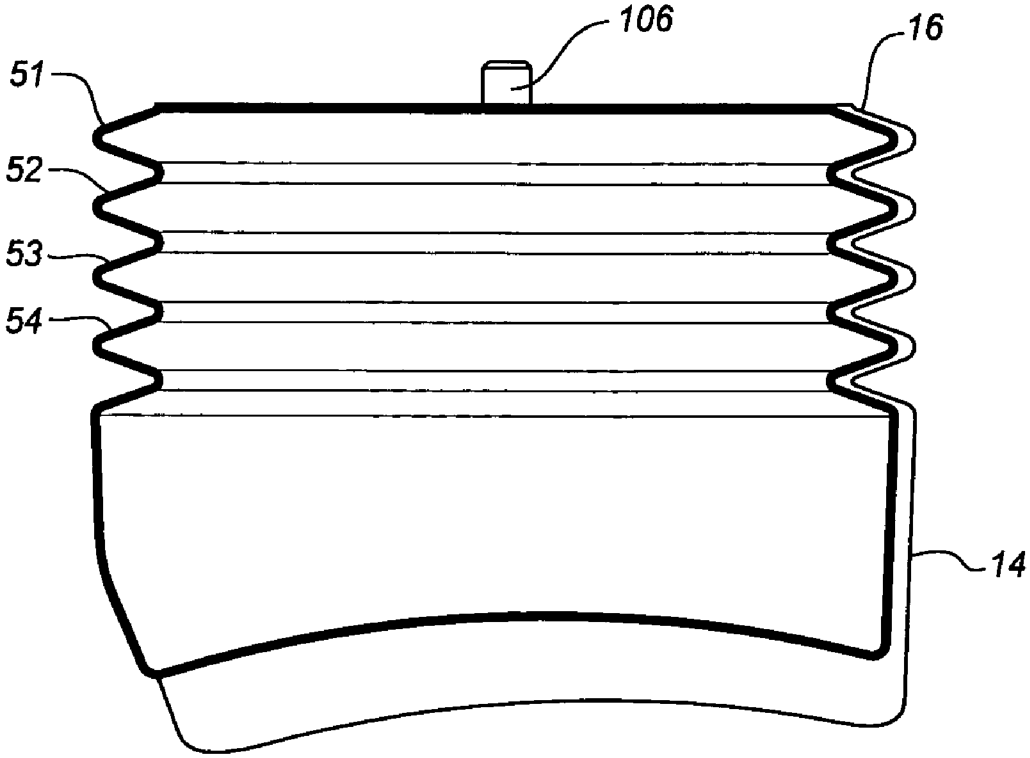
FIG. 4 is a cross-sectional view through an inflated bellows section of a cervical traction/stretch device constructed according to the teachings of the present invention.

By making the bellows section 16 with a non-elastic and non-stretching material, such as PVC, the air pressure will cause expansion of the bellows section 16, as shown in FIG. 4, and not inflation or stretching of the bellows section 16. Also, the actual air pressure in the bellows section 16 relative to actual stretch will be displayed on the pressure gauge 23.

Figure 2:
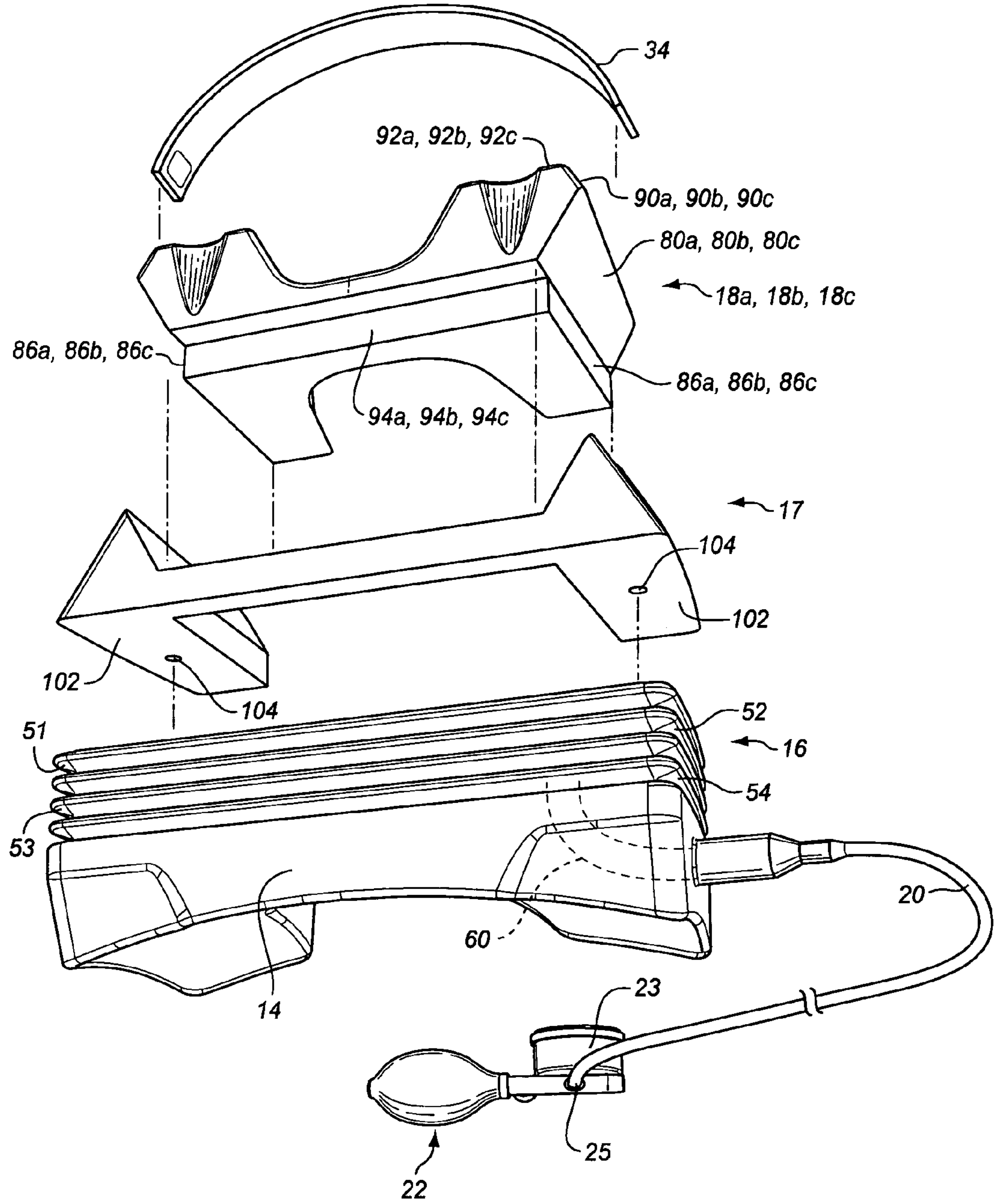
FIG. 2 is an exploded perspective rear view of the cervical traction/stretch device constructed according to the teachings of the present invention.

In the integral shoulder section 14 and bellows section 16, the shoulder section has a passage 60, shown in phantom in FIG. 2, for connecting the tubing 20 to the bellows section 16.

The bellows section 16 is generally rectangular and extends substantially the full height and width of the device 10. The bellows section 16 has a top side 56 and an arcuate, semi-circular or U-shaped surface 58 extending downwardly from the top side 56 generally aligned with a U-shaped surface 42 of the shoulder section 14 to provide a nesting support for a patient's neck.

Figure 5:
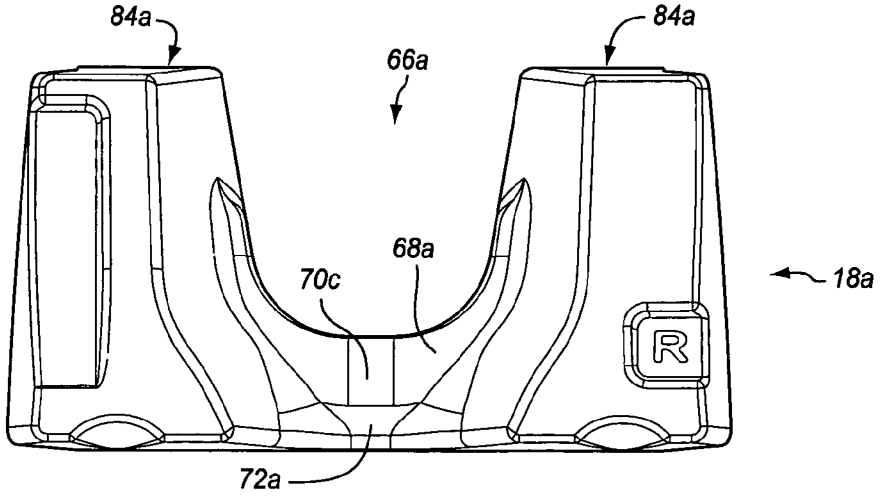
FIG. 5 is a top plan view of a regular size head section of the inflatable cervical traction/stretch device shown in FIG. 1.
Figure 6:
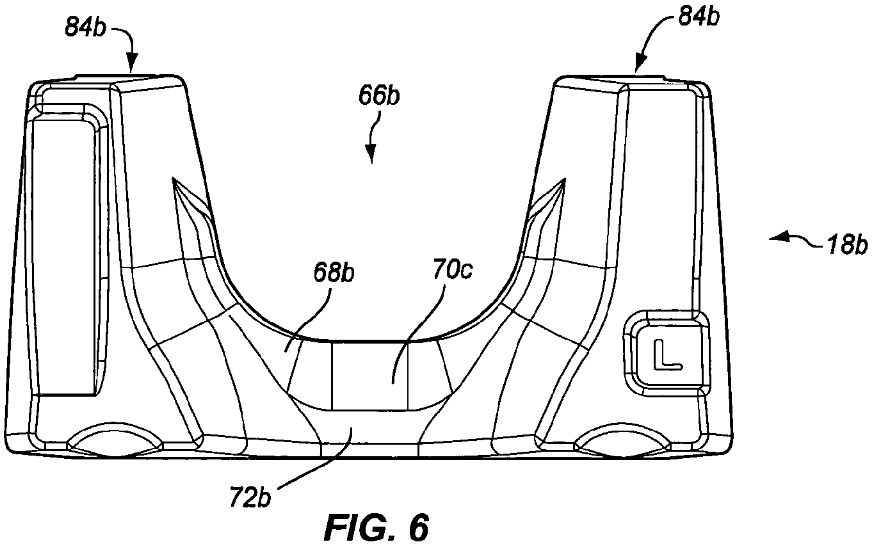
FIG. 6 is a top plan view of a large size head section of the inflatable cervical traction/stretch device shown in FIG. 1.
Figure 7:
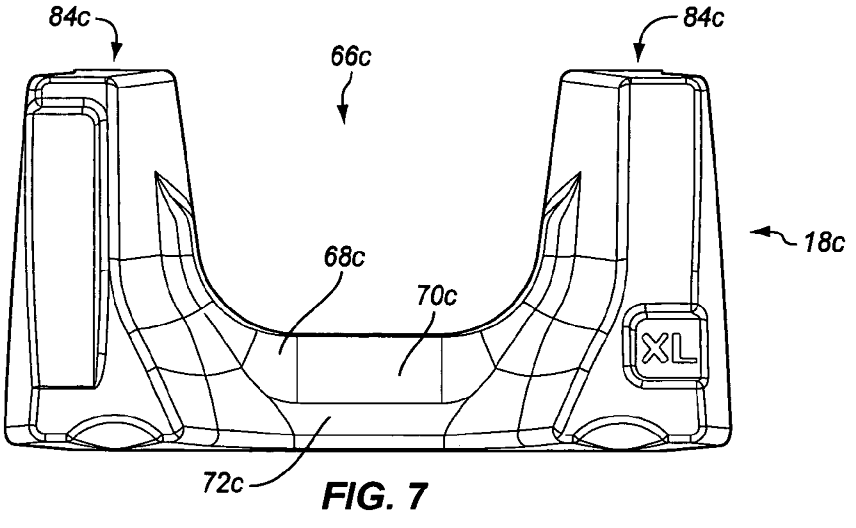
FIG. 7 is a top plan view of an extra large head section of the inflatable cervical traction/stretch device shown in FIG. 1.

A regular size head portion 18*a* is shown in FIG. 5. A large size head portion 18*b* is shown in FIG. 6. Finally, a wide size head portion is shown in FIG. 7. The head sections 18*a*, 18*b*, and 18*c* are made from polyurethane self-skinning foam.

Each head section 18*a*, 18*b* or 18*c* is generally rectangular in shaped and is formed with a generally U shape with a U opening 66*a*, 66*b* or 66*c* (for receiving the backside of a patient's head) at an upper or free end thereof and has a generally arcuate or semi-cylindrical U-shaped and inclined surface 68*a*, 68*b* or 68*c* having a surface portion 70*a*, 70*c* or 70*b* (see FIG. 3) that inclines slightly downwardly at the center to fit the cervical curve of the patient's neck and has a lower head receiving surface 72*a*, 72*b* or 72*c* having a center portion that curves downwardly for mating with the cervical curve.

The width of the U 66*b* and the U 66*c* is greater than the width of the U 66*a*. As shown in FIG. 6, the edge of the U 66*c* is less inclined in a horizontal direction than the edge of the U 66*b*. Also, the width of the portion 70*c* and the width of the surface 72*c* is less than the width the portion 70*b* and of the surface 72*c* which in turn is less than the width of the width the portion 70*a* and of the surface 72*a*. These slightly different constructions of the head sections 18*a*, 18*b* or 18*c* enables them to receive and accommodate heads of different size which are labeled as follows: head section 18*a*, R for regular; head section 18*b*, L for large; and head section 18*c*, XL for extra large.

With these three head sections 18*a*, 18*b* and 18*c*, the cervical/traction device kit can fit or can accommodate substantially all human heads or at least most of them.

As shown in FIG. 1 the device 10 has in the U-shaped openings and at the center of the U-shaped surfaces 42, 58 and 68*a* (FIG. 5), 68*b* (FIG. 6) or 68*c* (FIG. 7) curved straight or inclined surfaces including surfaces 68*a* (FIG. 5), 68*b* (FIG. 6) or 68*c* (FIG. 7) and 70*a* (FIG. 5), 70*c* (FIG. 7) or 70*b* (FIG. 6), for receiving the cervical curve of the neck. Then as one moves to the left side or the right side of the U-shaped openings in the area of the U-shaped opening in the head section 18*a*, 18*b* or 18*c*, the head receiving surface 72*a*, 72*b* or 72*c* has a pronounced shoulder, the occipital bone receiving surface and then a gentle sloping curving surface portion for supporting the head above the occipital bone on each side of the head. The surfaces 68*a*, 70*a* and 68*b*, 70*b* and 68*c* and 70*c* are shaped to grasp the occiput and mimic two hands manually supporting the head and gently pulling the occiput away from the shoulders when the bellows are filled thereby to optimize the grasp on the occiput and eliminate slippage.

As shown in FIG. 6, near a top side 81 of the head section 18*a*, 18*b* or 18*c*, the U-shaped surface 68*a*, 68*b* or 68*c* slopes in a longitudinal direction downwardly and merges in or with a smooth downwardly extending curved surface portion 82 of the head receiving surface 72*a*, 72*b* or 72*c* which extends to an outer end wall surface 84*a*, 84*b* or 84*c* of each head section 18*a*, 18*b* or 18*c* on each side of the head receiving surface 72*a*, 72*b* or 72*c*.

Figure 8:
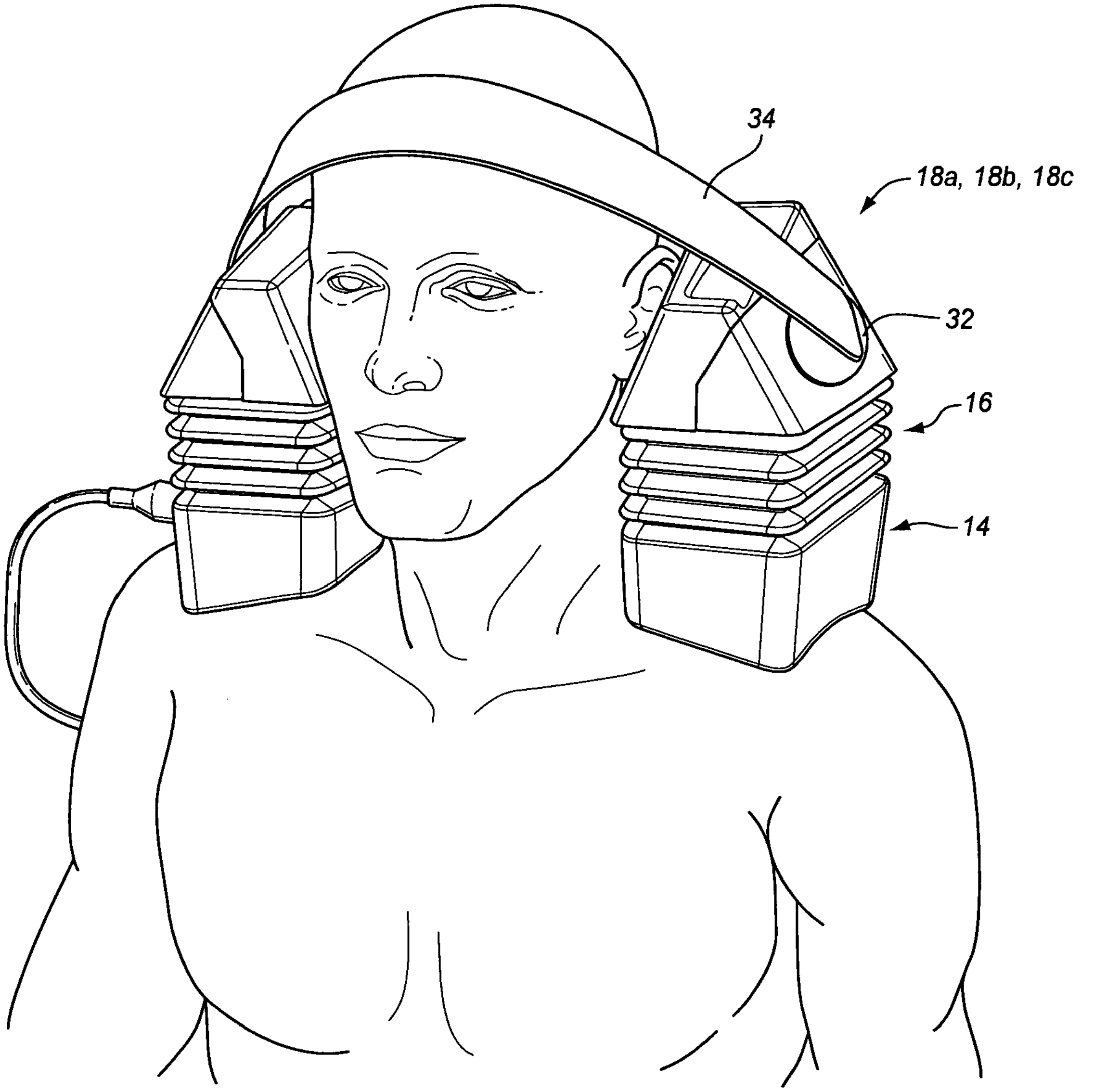
FIG. 8 is a perspective view of an upper portion of a human body lying horizontally with the head fixed in the cervical traction/stretch device of the present invention.

Then the ends of the head sections 18*a*, 18*b* or 18*c*, on either side of the center thereof, have left and right end wall surfaces 86*a*, 86*b* or 86*c* (FIG. 1) extending directly upwardly from a flat bottom of the head section 18*a*, 18*b* or 18*c* to an outwardly or laterally outwardly and upwardly extending inclined intermediate wall surfaces 88*a*, 88*b* or 88*c* to an inwardly inclined wall surface 90*a* (FIG. 2), 90*b* or 90*c* to an upper flat top surface 92*a*, 92*b* or 92*c*. As shown in FIGS. 6 7 and 8 the end wall surfaces 84*a*, 84*b* or 84*c* extend downwardly to a stepped shoulder that extends inwardly to a flat, lower wall surface 94*a*, 94*b* or 94*c* (FIG. 2). All of the lower wall surfaces 86*a*, 86*b* or 86*c* and 94*a*, 94*b* or 94*c* and the intermediate wall surfaces 88*a*, 88*b* or 88*c* are constructed and arranged to fit into matching or mating surfaces of the head frame as described below.

As best shown in FIG. 1 and in FIG. 2, the head frame 17 includes two opposed and spaced apart trapezoidal and partially triangular side block portions 96 which are connected by a generally rectangular in cross section bar 98. As shown, the head frame has a U shaped opening 100 defined by opposed, facing inner wall surfaces 98 (which mate with or abut lower wall surfaces 86*a*, 86*b* or 86*c* of each of the head sections 18*a*, 18*b* or 18*c*) and an inner wall surface 98 on the bar 98 (which mate with or abut the lower wall surfaces 94*a*, 94*b* or 94*c* of the head sections 18*a*, 18*b* or 18*c*).

The lower wall surfaces 86*a*, 86*b* or 86*c* of each of the head sections 18*a*, 18*b* or 18*c* and the lower wall surfaces 94*a*, 94*b* or 94*c* of the head sections 18*a*, 18*b* or 18*c* have identical measurements and form an identical base structure for being received in the U shaped opening 100 and constitute an interchangeable base structure for the head sections 18*a*, 18*b* or 18*c*.

The head frame 17 has a bottom wall surface 102 having spaced apart holes 104 as shown in FIG. 2 which are adapted to realesably and frictionally receive spaced apart prongs or projections 106 on an outer surface 108 of the bellows section 16 as shown in FIG. 1.

So, in use, one of the head portions 18*a*, 18*b* or 18*c* is received and frictionally held in the head frame 17 which is fixed to the bellows section 16 by the frictional engagement of the prongs or projections 106 in the holes 104 and the thus constructed cervical traction/stretch device is laid on a flat, usually horizontal, surface ready for use by a patient as shown in FIG. 8.

Figure 9:
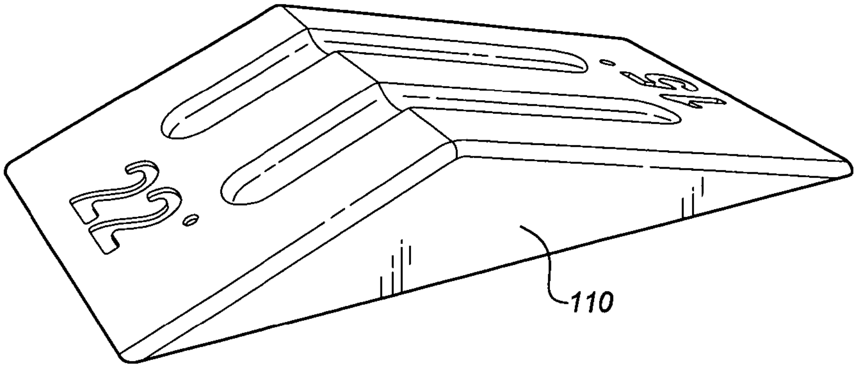
FIG. 9 is a perspective view of a triangular-cross-section base stand for supporting the cervical traction/stretch device of the present invention at a small angle to the horizontal.
Figure 10:
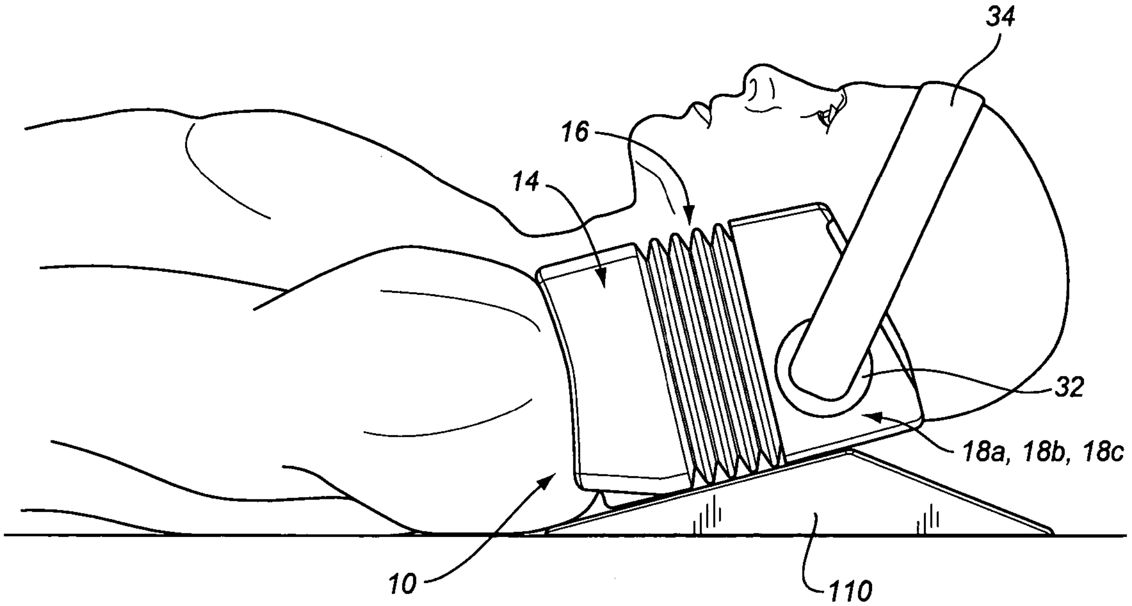
FIG. 10 is a side plan view of the cervical traction/stretch device shown in FIG. 1 positioned on base stand with the neck of a patient resting therein, placing traction on the patient's neck.

It has been found that for some patients, positioning of the cervical traction/stretch device at a slight angle, 5-30 degrees, preferably 15 degrees to the horizontal provides better relief to the patient by increase of the initial stretch or bend of the neck. So, the kit includes a triangular in cross section base stand 110 as shown in FIG. 9. A patient using the base stand is shown in FIG. 10.

In use, the patient assembles the best fitting head section 18*a*, 18*b* or 18*c* into a cervical traction/stretch devise 10, lays it on the floor or on the base stand 110, fixes the head strap 34 over the temple of the head of the patient, and starts pumping the hand pump/bulb 22 until a maximum pressure or level of pain relief has been reached. The patient then lays there for a recommended time period to effect relief of his or her pain.

The cervical/traction device kit including three interchangeable head sections 18*a*, 18*b* and 18*c* provides a generally universally usable cervical traction/stretch device. The non-elastic and non-stretchable, but expandable, bellows section enables proper stretching of the neck at a correct pressure. Finally, the base stand 110 enables the neck to be bent slightly while using the cervical traction/stretch device to stretch the cervical portion of the neck/spine.

From the foregoing description, it will be apparent that the cervical traction/stretch device kit including the cervical traction/stretch device 10 of the present invention has a number of advantages, some of which have been described above and others of which are inherent in the invention. For example, the use of non-stretching and non-elastic material for the bellows allows the pressure in the bellows section to be gauged accurately and the three head sections provide a "universal" cervical traction/stretch device kit, one which can be used for almost every head size.

Also from the foregoing description it will be apparent that modifications can be made to the cervical traction/stretch device kit and the cervical traction/stretch device 10 without departing from the teachings of the invention.

What is claimed is:

1. A cervical traction/stretch device comprising:

an expandable bellows section made of non-elastic and non-stretchable material;

at least two head sections for accommodating different sized human heads and having an identical base;

a head frame having receiving structure for receiving one of the at least two head sections at a time and having mating engaging structure for frictionally and releasably attaching to the bellows section;

a shoulder section fixed to or made integral with the bellows section; and a pumping mechanism for expanding the bellows section, wherein the at least two head sections, the bellows section, and the shoulder section each include a U-shaped opening therein adapted to receive and support a patient's neck, the U-shaped openings being aligned when one of the at least two head sections is attached to the bellows section.

2. The cervical traction/stretch device of claim 1, wherein said pumping mechanism includes an air pump and an air relief structure coupled to the bellows section for pumping air into the bellows section and for relieving or releasing air out of the bellows section.

3. The cervical traction/stretch device of claim 1, wherein said non-elastic and non-stretchable material is PVC.

4. The cervical traction/stretch device of claim 1, wherein said non-elastic and non-stretchable material is P130 Plastisol having a 70-80 durometer on the Shore A scale.

5. The cervical traction/stretch device of claim 1, wherein each of the at least two head sections is made of polyurethane foam.

6. The cervical traction/stretch device of claim 1, further including a base that is triangular in cross section for supporting the cervical traction/stretch device at a small angle to the horizontal.

7. The cervical traction/stretch device of claim 6, wherein the base includes at least one side for supporting the cervical traction/stretch device and said angle of the at least one side is between 5 and 30 degrees to the horizontal.

8. The cervical traction/stretch device of claim 1, wherein the bellows section includes a plurality of undulations.

9. The cervical traction/stretch device of claim 1, wherein at least a first head section, a second head section, and a third head section are provided.

10. The cervical traction/stretch device of claim 9, wherein each head section has head receiving surfaces surrounding the U-shaped opening in each head section, the U-shaped opening in the second head section having a width greater than the U-shaped opening in the first head section, and the U-shaped opening in the third head section having a width greater than the U-shaped opening in the second head section.

11. The cervical traction/stretch device of claim 10, wherein the head receiving surfaces of the first head section, the second head section, and the third head section have slightly different configurations to accommodate human heads of different size.

12. The cervical traction/stretch device of claim 9, wherein the first head section is of a greater thickness than the second head section and the second head section is of a greater thickness than the third head section.

13. The cervical traction/stretch device of claim 1, further comprising a strap adapted to be received over a patient's head and secured to the head frame.

14. A method for applying cervical traction/stretch comprising:

attaching a head frame to an expandable bellows section, the head frame having receiving structure for receiving one head section at a time and having mating engaging structure for frictionally and releasably attaching to the expandable bellows section, and the expandable bellows section being fixed to or made integrally with a shoulder section;

selecting one of at least two head sections, the at least two head sections having an identical base for being received on the head frame but being configured to accommodate different sized human heads;

attaching the selected one head section to the head frame; and operating a pumping mechanism to expand the bellows section, wherein the at least two head sections, the head frame, the bellows section, and the shoulder section each have a U-shaped opening therein adapted to receive and support a patient's neck, the U-shaped openings being aligned when one of the at least two head sections is attached to the bellows section.

15. The method for applying cervical traction/stretch of claim 14, wherein the bellows section includes a plurality of undulations.

16. The method for applying cervical traction/stretch of claim 14, further including a step of supporting the cervical traction/stretch device at a small angle to the horizontal with a base that is triangular in cross section.

17. The method for applying cervical traction/stretch of claim 16, wherein the base supports the cervical traction/stretch device at an angle between 5 and 30 degrees to the horizontal.

18. The method for applying cervical traction/stretch of claim 14, further comprising a step of placing a strap over a patient's head to secure the patient's head to the head frame.

19. The method for applying cervical traction/stretch of claim 14, wherein each of the at least two head sections is made of polyurethane foam.

20. The method for applying cervical traction/stretch of claim 14, further comprising a step of placing a base behind the selected one head section, the head frame, the expandable bellows, and the shoulder section for supporting the patient's neck at a small angle to the horizontal.

* * * * *